United States Patent
Costley et al.

(10) Patent No.: US 6,581,466 B1
(45) Date of Patent: *Jun. 24, 2003

(54) ACOUSTIC INSPECTION OF STRUCTURES

(75) Inventors: R. Daniel Costley, Oxford, MS (US); Mark E. Henderson, Long Beach, MS (US); Gary N. Dion, Madison, AL (US)

(73) Assignee: Mississippi State University, Mississippi State, MS (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/539,553

(22) Filed: Mar. 31, 2000

Related U.S. Application Data

(60) Provisional application No. 60/127,481, filed on Apr. 2, 1999.

(51) Int. Cl.[7] ............................................... G01N 29/04
(52) U.S. Cl. ........................... 73/584; 73/597; 73/598; 73/602; 73/643
(58) Field of Search ......................... 73/584, 588, 639, 73/649, 803, 598, 599, 602, 640, 643, 600, 597

(56) References Cited

U.S. PATENT DOCUMENTS

| | | | | |
|---|---|---|---|---|
| 3,762,496 A | * | 10/1973 | Milberger et al. | 73/588 |
| 3,937,065 A | * | 2/1976 | Milberger et al. | 73/588 |
| 4,184,374 A | * | 1/1980 | Thompson et al. | 73/640 |
| 5,165,270 A | * | 11/1992 | Sansalone et al. | 73/572 |
| 5,456,113 A | * | 10/1995 | Kwun et al. | 73/587 |
| 5,457,994 A | * | 10/1995 | Kwun et al. | 73/587 |
| 5,814,731 A | * | 9/1998 | Alexander et al. | 73/644 |
| 6,055,862 A | * | 5/2000 | Martens | 73/632 |
| 6,119,526 A | * | 9/2000 | Reigstad et al. | 73/803 |
| 6,381,547 B1 | * | 4/2002 | Heirtzler et al. | 702/39 |

OTHER PUBLICATIONS

"Standard Practice for Measuring Delaminations in Concrete Bridge Decks by Sounding", ASTM Designation: D4580—86 (Reapproved 1992), pp. 1–3.

"Operators Manual for the SIE Delamtect", believed to be prior to Jan. 1, 1999.

Henderson, M.E., et al., "Acoustic Inspection of Concrete Bridge Decks", Diagnostic Instrumentation and Analysis Laboratory, Starkville, MS, Mar. 3, 1999.

* cited by examiner

Primary Examiner—Daniel S. Larkin
Assistant Examiner—Jacques Saint-Surin
(74) Attorney, Agent, or Firm—Piper Rudnick LLP; Steven B. Kelber

(57) ABSTRACT

A method for inspecting concrete structures includes the steps of exciting the structure to be inspected with a mechanical device such as a chain, sensing resulting vibrations with an acoustical sensor such as a microphone that is not physically coupled to the structure, processing the received signals to exclude signals with frequencies outside of response frequencies of interest corresponding to defects desired to be detected, and examining the received signals. In preferred embodiments, the mean square of the processed signals are compared to a threshold. Areas for which the total energy across the frequency bands of interest exceeds the threshold correspond to defects such as delaminations. The received signals are collected from various locations on the structure. In preferred embodiments, the location of the received signals is also maintained. Also provided is an apparatus for inspecting concrete structures that comprises a mobile platform, such as a wheeled cart or trailer, to which is mounted an excitation device such as a chain, a microphone for receiving acoustic signals from the structure, and a computer for analyzing signals from the microphone.

29 Claims, 3 Drawing Sheets

ACOUSTIC INSPECTION OF STRUCTURES

This application claims priority to U.S. Provisional Application Ser. No. 60/127,481, filed Apr. 2, 1999, which is incorporated herein by reference in its entirety.

BACKGROUND OF THE INVENTION

1. Field of the Invention

The present invention is related to the inspection of structures, and more particularly to nondestructive inspection of structures accomplished through analysis of sound waves from the structure.

2. Related Art

Many of our nation's bridges and other similar structures are aging rapidly. As a consequence, it has become increasingly important to determine the structural integrity of concrete structures such as concrete bridge decks. Known systems and methods for testing concrete structures are expensive, slow or tedious.

One problem of particular concern is the detection of concrete delamination. Concrete delamination is the separation of a concrete structure into two or more layers. Most concrete structures, such as bridge decks, employ reinforcing bar (referred to herein as rebar) for structural strength. In a structure such as a bridge deck, it is customary to lay the rebar in a grid pattern approximately two inches below the surface of the concrete. The location of the rebar is also frequently the location of delamination. The delamination occurs when water comes into contact with the rebar, causing it to corrode. Because corrosion is an expansive process, the rebar acts as a wedge that splits the concrete into layers.

Some of the earliest techniques for locating delamination in concrete bridge decks involve either tapping on the surface of the bridge deck with a hammer or metal rod or dragging a chain bar across the bridge deck. A clear ringing sound is produced by an intact, healthy structure. However, where a delamination exists, a dull hollow sound is heard. These techniques have the advantage of being simple and inexpensive. They allow inspectors to inspect large structures in a shorter amount of time than is possible with some other nondestructive testing techniques, such as ultrasonic pulse-velocity methods. However, these techniques have the disadvantages of (a) relying on the suggestive interpretation of the inspector; and (b) being difficult to implement in noisy environments, such as inspecting one lane of a bridge deck while traffic is driving in the other lanes.

Some state of the art systems use ground penetrating radar to locate defects such as delamination. These systems have inherent problems, especially with ghosting and signature overlap. These systems are often prohibitively expensive as well. Other non-destructive techniques, such as ultrasonic pulse-velocity, suffer from similar drawbacks.

Another known device, which is referenced in ASTM Standard Practice D4580-86, "Standard Practice for Measuring Delaminations in Concrete Bridge Decks by Sounding," involves impulse excitation and the use of piezo-electric hydrophones to detect defects. The hydrophones are enclosed in a soft, oil-filled tire which is mounted on a mobile cart. The hydrophones are mounted inside the tire such that they are in close proximity to the concrete but do not rotate when the tire rotates. The hydrophones are physically coupled to the concrete through the soft tires and the oil in the tires. Properly calibrating and maintaining this device has proven problematic. Another problem occurs when using this device over the grooves commonly cut into concrete bridge decks today. This problem is a result of the device's reliance on physical coupling between the sensor and the surface.

What is needed is a simple and inexpensive method for inspecting concrete structures that does not rely on the subjective interpretation of an human inspector.

SUMMARY OF THE INVENTION

The aforementioned needs are met to a great extent by the present invention, which provides a method for inspecting concrete structures in which characteristics of a signal from a structure of known quality are compared to characteristics of an unknown signal. In one embodiment of the invention, a distance measurement is used to compare the two signals. The distance measurement is then used an indicator. The distance measurement, or indicator value, is then thresholded and the result is a yes/no decision or a variable where value is an indicator of quality. The comparison and generation of the indicator value can be performed using autonomous learning techniques such as artificial neural networks, transform spaces such as, but not limited to, Linear Prediction Coefficients or Cepstral Coefficients, through direct filtering methods, or through frequency domain comparisons. The characteristics of a known structure can be compiled from a database which averages the characteristics from among many samples (which may include both high quality and low quality structures).

A preferred embodiment of the invention includes the steps of exciting the structure to be inspected with a mechanical device such as a chain, sensing resulting vibrations with a sonic receiver, such as a microphone, not physically coupled to the structure, processing the received signals to exclude signals with frequencies outside of a range of response frequencies corresponding to defects desired to be detected, and comparing the processed signals to a threshold. Areas for which the energy across the frequency bands of interest exceeds the threshold correspond to defects such as delaminations. The received signals are collected from various locations on the structure. In preferred embodiments, the location of the received signals is also maintained. The location may be obtained through use of a device such as an odometer or a differential global position sensor (DGPS).

The invention also provides an apparatus for inspecting concrete structures. In preferred embodiments the apparatus comprises a mobile platform, such as a wheeled cart or trailer. A chain bar, which is a horizontal bar that includes several chains, preferably of equal length, attached to it is mounted to the cart such that the chains drag along the structure to be inspected when the mobile platform is moved. A microphone is attached to the mobile platform and positioned such that it preferentially receives sounds generated by the excitation source on the surface under test. The signals received by the microphone are then converted to digital form by a data conversion device and input to a processor. The processor then processes the signals to exclude signals corresponding to frequencies outside of the desired frequency range and compares the processed signals to a threshold. Also attached to the processor is a position sensing device such as an odometer or DGPS. The processed data is output to an output device, which is a chart recorder or a computer display in preferred embodiments. Both raw and processed data are also stored in preferred embodiments. The raw data may be used for archival and/or training purposes, or for post-processing.

In a highly preferred embodiment, results are displayed in a plan view format in a graph in which a horizontal axis represents position along a length of the structure, a vertical axis represents position along a width of the structure, and the energy from the frequencies of interest is indicated by color. Positions on the structure at which the energy falls below a threshold are not displayed in such embodiments.

An aspect of the invention is that it is more robust because the acoustical sensor is not physically coupled to the structure to be tested. Another aspect of the invention is the automation of the detection process through the comparison of the received energy to a threshold. Still another aspect of the invention is the ability to process the acoustical data and locate defects in real time. This aspect allows defects to be marked on the structure when the defects are detected in some embodiments.

These and other aspects, advantages and features of the present invention can best be understood with reference to the drawings and accompanying description herein.

DETAILED DESCRIPTION OF THE INVENTION

The present invention will be discussed with reference to preferred embodiments of methods and apparatuses for detecting defects in concrete structures. The invention is believed to be particularly well suited for detecting delaminations in concrete bridge decks and therefore will be discussed in connection with detecting delaminations. It will be appreciated that the invention may be used to detect other types of defects as well. Specific details, such as excitation frequencies, types of transforms performed on received signals, etc., are set forth in order to provide a thorough understanding of the present invention. The preferred embodiments discussed herein should not be understood to limit the invention.

Figure 1:
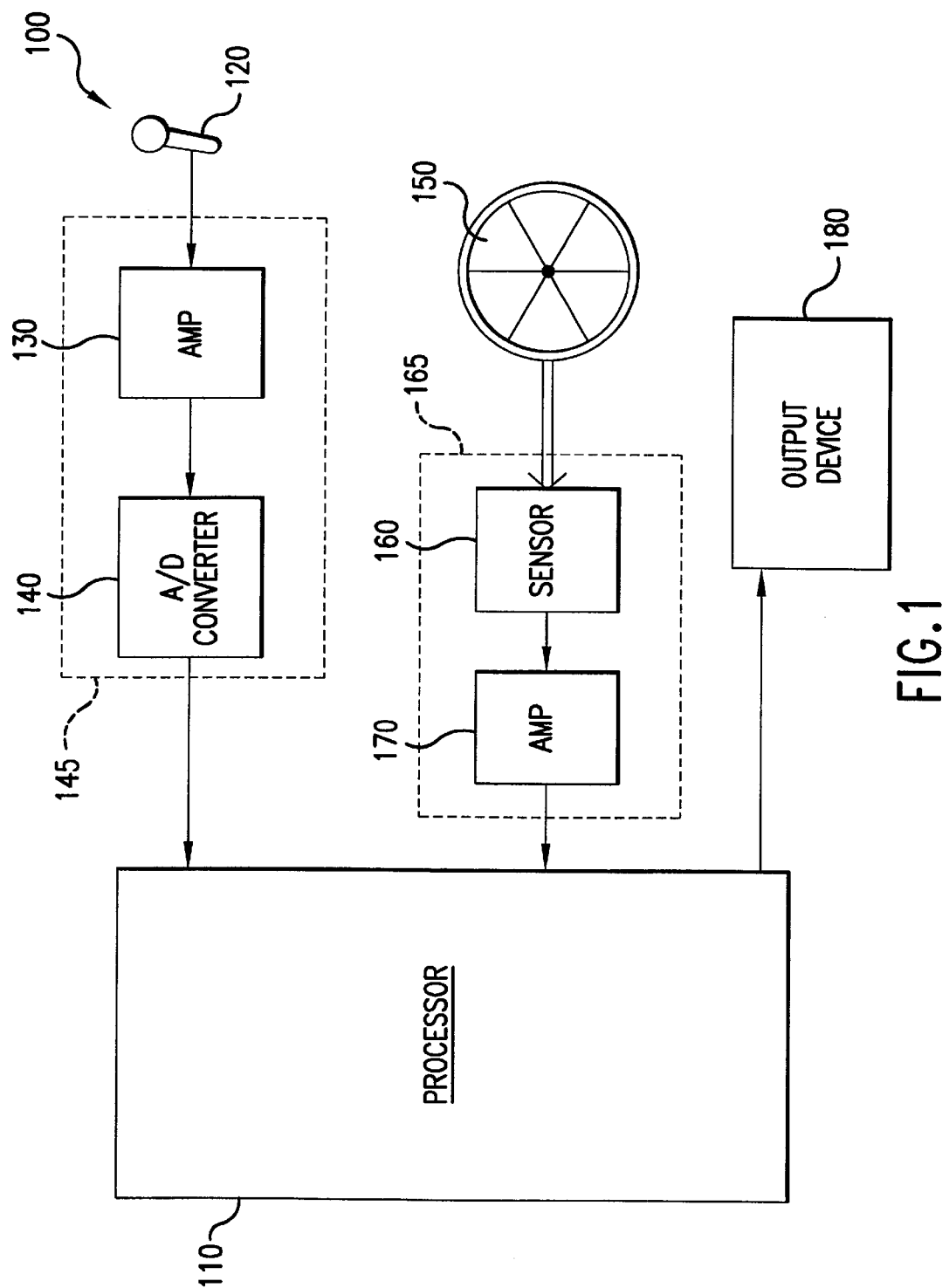
FIG. 1 is a block diagram of a concrete structure inspection apparatus according to a preferred embodiment of the present invention.

A hardware block diagram of a preferred embodiment of a system 100 for detecting delaminations is illustrated in FIG. 1. Although not shown in FIG. 1, the system 100 includes a device in physical contact with a section of the bridge deck to be inspected such that the section is excited and defects can be detected.

The mechanism by which a sound is produced by a delamination is complex and not completely understood. The following discussion sets forth one way to select the excitation necessary to detect the delamination. It should be understood, however, that the following discussion is theoretical only.

In order to detect a delaminated section of a bridge deck, the section should be excited (i.e. vibrated) at its fundamental frequency. According to classical plate theory, the fundamental frequency of a circular plate is given by:

$$\omega_{fundamental} = \beta_{fundamental}^2 \, (\pi h / 2r^2) \sqrt{\frac{E}{3\rho(1-\mu^2)}} \quad (1)$$

where β is the eigenvalue of the fundamental frequency (1.015 for the fundamental frequency), E is the modulus of elasticity (25 Gpa for concrete), $\mu$ is Poisson's ratio (typically 0.1 to 0.2 for concrete), ρ is the density of the material (2600 kg/m$^3$ for concrete), h is the thickness of the plate, and r is the radius of the plate. Using equation 1, and fixing the depth of the delamination (the thickness of the plate) at two inches, Table 1 lists the fundamental frequency for various sized circular delaminations:

TABLE 1

| Radius (cm) | Fundamental Frequency (Hz) |
| --- | --- |
| 1 | 1488607 |
| 5 | 59544 |
| 10 | 14886 |
| 15 | 6616 |
| 20 | 3722 |
| 25 | 2382 |
| 30 | 1654 |
| 35 | 1215 |
| 40 | 930 |
| 45 | 735 |
| 50 | 595 |

Table 1 illustrates two important points. First, the acoustical sensor must have a fairly broad band to detect the defects/frequencies of interest. Second, the excitation source must also have a fairly broad band. Through testing, it has been determined that a frequency range from approximately 500 Hz to approximately 6000 Hz is effective for detecting delaminations of the sizes indicated in Table 1. This is the frequency range used in preferred embodiments. However, testing also suggests that other frequency ranges, such as the 20 kHz to 60 kHz range, also contain useful information. Frequencies above this range are not preferred because air is not a good coupling medium at such frequencies and thus signals received from a microphone are difficult to amplify sufficiently for analysis.

Producing the required excitation can be accomplished in several ways. One possibility is to excite using an impulse load such as a hammer strike. This method has the advantage of having a very wide spectral content, but results in information about the structure only in locations where the strike occurs, thereby raising the possibility that small defects could be overlooked. A second method for exciting the structure, used in preferred embodiments, is to excite the structure with broadband noise such as by dragging a set of chains across it. This produces noise that is both spectrally and spatially diverse. The spectrum of noise is quite broad and, because the chains are dragged across the entire deck, small defects will not be overlooked. In preferred embodiments, several spaced-apart lengths of chain are used. Preferably, the chain diameters range from 3/16" to 1/2." Highly preferred embodiments employ 5–6 lengths of 3/8" diameter chain separated from each other by approximately two inches.

While the section of the bridge deck to be inspected is being excited, a microphone 120 positioned near the deck section receives acoustic waves produced by the excited deck section. The microphone is preferably unidirectional such that acoustic waves from the section are preferentially received. The microphone preferably has a bandwidth of approximately 70 Hz to at least approximately 15 kHz. The signals from the microphone 120 are input to a processor 110 through a data distribution device 145, which comprises an amplifier 130 and an A/D converter 140 in preferred embodiments. The A/D converter may take the form of a peripheral card that can be attached to a personal computer. An example of such a card is a National Instruments data acquisition card having 16 channels and a sample rate of 44.1 K samples/sec.

The processor 110 inputs the digitized acoustic signals and groups them over some period of time, or time window. In preferred embodiments, groups consist of 4096 samples, which is a 93 millisecond time interval. The time window was chosen to provide good resolution while not overburdening the processor 110. Next, the processor 110 processes them to remove signals outside the frequencies of interest. In preferred embodiments, the frequencies of interest range from approximately 500 Hz to approximately 6 kHz, which corresponds to circular delaminations having a radius from approximately 15 to 50 cm as discussed above. In preferred embodiments, the processing consists of digitally filtering the data. Of course, those of skill in the art will recognize that other schemes, such as passing the signals through an analog bandpass filter prior to passing them through the A/D converter or transforming them to the frequency domain (e.g. Fourier transform) and then filtering in the frequency domain, are also possible.

Next, the processed signal is squared and the mean of the squared signal, or the mean squared value, is calculated and compared to a threshold. The mean square value represents the signal energy. (Those of skill in the art will recognize that other representations of the signal energy may also be used.) If the mean square value exceeds the threshold, delamination has been detected. In preferred embodiments, the resulting average from each time window is displayed in real time on an output device 180 such as a monitor attached to the processor 110.

In order to inspect large objects such as concrete decks, it is necessary to excite various portions of the deck. In preferred embodiments (discussed in further detail below), the system is mounted on a mobile wheeled platform and moved across the surface of the deck. In such embodiments, it is preferable to map the time window discussed above to a location of a corresponding section of the bridge deck. One way to accomplish this mapping is to connect an odometer 165 mounted on one of the wheels 150 of the mobile platform to the processor 110. The odometer 165 (which includes a sensor 160 and A/D converter 170) signals the processor each time the wheel is moved a distance of, for example, nine inches. The processor records the time of each odometer click so it can be correlated with a time window. The same result may be accomplished using a DGPS.

In the embodiment described above, the mobile platform may be moved across the surface at a non-constant rate, such as when pushed by a human being. Because the rate at which the microphone is sampled does not depend upon the rate at which the mobile platform is moved, this will result in equally sized portions of the structure having different numbers of time windows of data. In other words, for each nine inch bridge deck section, approximately 2.5 time windows of data will be collected if the platform is moved at 2.5 miles/hour, the sample rate is 44.1 kHz, and each time window contains 4096 samples. If the rate at which the platform is moved varies, some 9" sections will have only a single time window of data, while others will have 2 or 3 time windows of data. This difference can be compensated for by simply averaging the mean square across multiple time windows for each nine inch section. In cases where a time window extends from one nine inch section to another, the data from that time window may be discarded.

In highly preferred embodiments, a two dimensional plan view of the deck is constructed. The platform is moved across the length of the deck to be inspected in successive passes starting at one end of the deck and continuing until the entire deck has been inspected, much in the manner one would mow a lawn. The starting position of each pass is recorded. The results are graphed such that the horizontal axis represents a position along the length of the deck while the vertical axis represents a position along the width of the deck. The average energy may be represented by colors or gray level on the graph.

In addition to the methods described above, automated or "learning" methods may also be used. Such techniques require no prior knowledge to extract information from the signal other than the knowledge that certain sections are known to be good and/or certain sections are known to be bad. Such techniques develop a signature reading from a good section of concrete and then use that signature to analyze subsequent sections of concrete. There are advantages to these types of methods as compared to the direct methods in that subtle changes over time can be accounted for, as can unknown dependencies that change from one trial to another.

An example of such an automated method uses linear prediction coeffecients (LPC) to characterize the signal from a good section of concrete. LPC is used extensively in the speech recognition field for its ability to characterize a stationary random signal as an all-pole filter. Given a white noise signal source that is passed through an all pole system, the LPC filter coefficients will match the poles in the system. By inverting the system and filtering by those coefficients, the signal will be 'whitened,' i.e., the part of the signal that is modeled by the coefficients will be removed. The part of the signal that is not modeled by the coefficients, the defect, remains.

Figure 2:
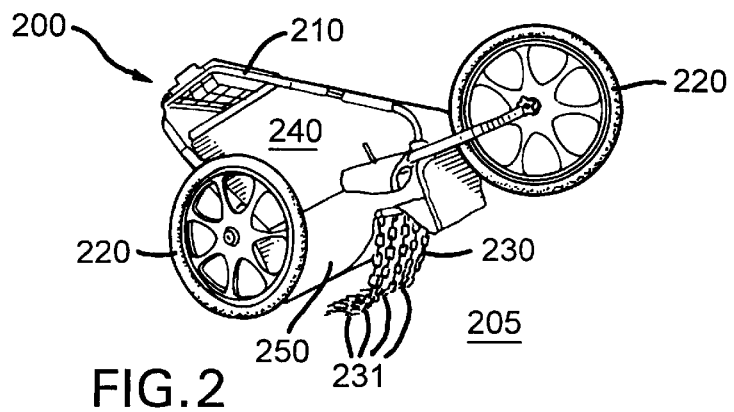
FIG. 2 is a perspective view of an inspection system according to a preferred embodiment of the present invention.
Figure 3:
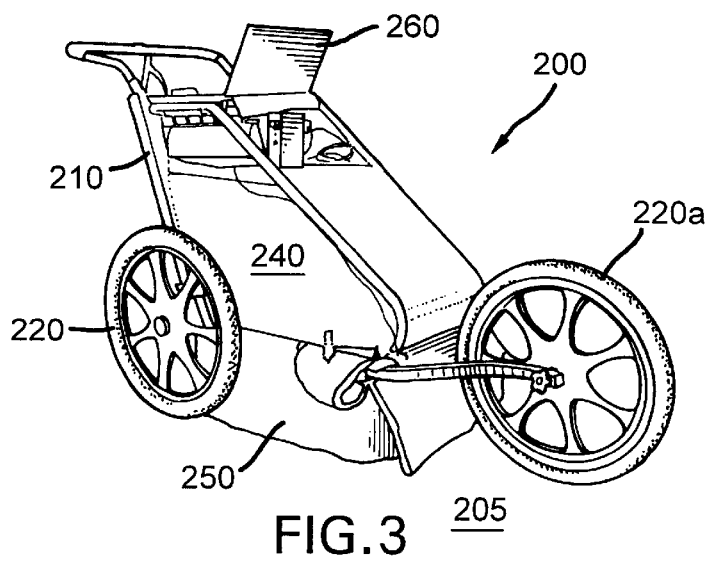
FIG. 3 is a second perspective view of the embodiment of FIG. 2.
Figure 4:
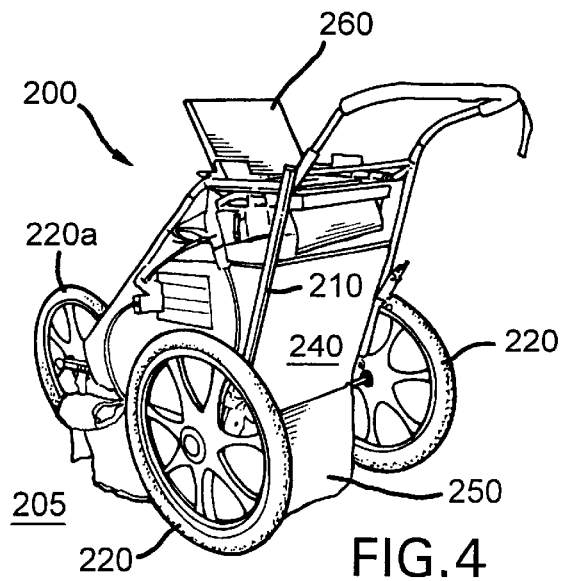
FIG. 4 is a third perspective view of the embodiment of FIG. 2.

FIGS. 2–4 illustrate a mobile system 200 according to a preferred embodiment of the present invention. The mobile system 200 includes a frame 210 and wheels 220 that may be taken from a popular type of child carrier commonly used by recreational joggers. The frame 210 is primarily comprised of 1" aluminum tubing. The wheels 220 are 20" diameter pneumatic tires. Hanging from the underside of the frame 210 is a chain bar 230 that includes five lengths of ⅜" chain 231. The chain lengths 231 are sufficiently long such that they are dragged along a surface over which the mobile system is moved, thereby exciting the surface. Above the chain bar 230 is a sound dampening barrier in the form of a box 240. The box 240 is constructed of R-board, which is a ¾" foam material coated with a thin layer of fiberglass on both sides. A microphone (not shown in FIGS. 2–4) is mounted inside the box 240. The microphone is a directional condenser microphone that is pointed down at the chains and deck surface to receive acoustic signals from the surface. Lining the interior of the box 240 is two inches of textured foam, which provides additional sound-dampening that creates an anechoic-like chamber, thus assuring that the microphone receives sound entering through the bottom of the box 240. A curtain felt 250 is provided around the bottom edge of the box 240 and extends downward to contact the surface 205. The curtain 250 also helps to keep noise from outside the box 240 from being received by the microphone.

On top of the box 240 is a computer 260, which is a Pentium laptop in this embodiment. The computer 260 is equipped with a PCMCIA data acquisition card of the type described above. The signal from the microphone is amplified to +/−5 volts and routed to the data acquisition card to take advantage of the full range of the A/D converters on the data acquisition card. The front wheel 220a is also equipped with a magnetic reed-type spoke sensor (not shown in FIGS. 2–4). The output of the sensor is also routed to the data acquisition card on the computer 260. The sample rate for both signals is 44.1 kHz, which provides CD-quality sound and is a common playback rate on many computers.

Figure 5:
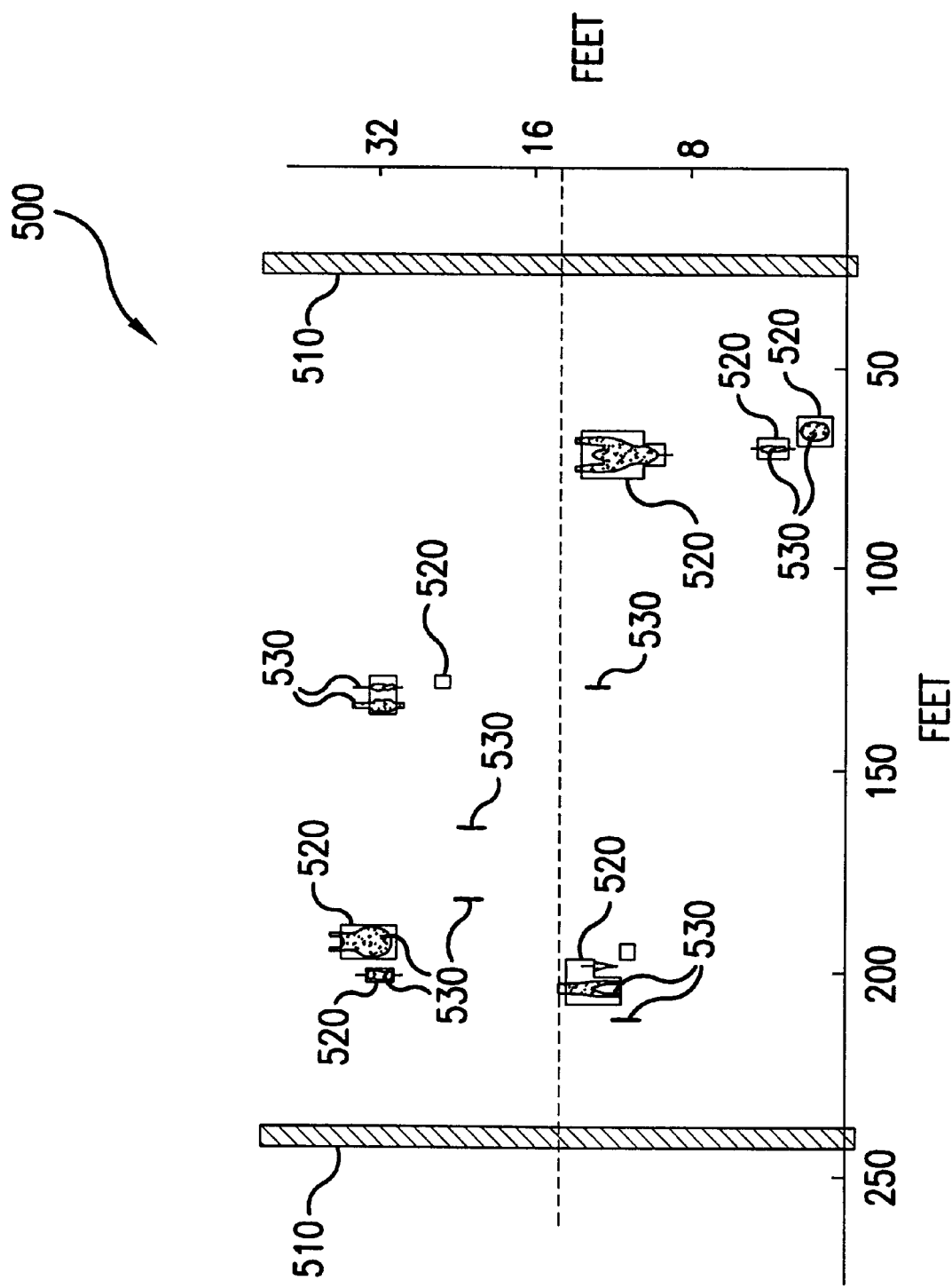
FIG. 5 is a graph showing defects detected by an embodiment of the invention and defects detected by a human inspector.

An embodiment of the invention has been built and tested on an actual bridge deck. The results of the test are displayed on a map-type graph 500 of the type discussed above as shown in FIG. 5. The data displayed on the graph 500 has been thresholded such that no data is displayed for non-defective areas. The large blocks 510 correspond to metal expansion joints in the bridge deck. The blocks 510 may be used to "line up" multiple passes of data. The block-shaped areas 520 are delamination areas detected by a human inspector. The irregularly shaped areas 530 are threshold crossings corresponding to defects detected by the invention.

The embodiment discussed above uses a push-cart as the mobile platform. However, a trailer may be used in place of the push cart in other embodiments. A trailer would allow the invention to be towed by a truck over a bridge deck under inspection. The width of the mobile platform may also be varied. For example, in a trailer embodiment, the width may be set approximately equal to the width of a traffic lane. This would allow an entire lane of the bridge deck to be inspected in one pass.

Other embodiments of the invention may be much smaller and narrower and may not employ wheels at all. For example, an embodiment of the invention approximately the size of a push broom may be constructed. In such an embodiment, the operator would pass the device over an area to be inspected. The device may sound an audible alarm when a delamination has been detected. Such an embodiment would be useful to a contractor or a construction crew in locating the outline of a delamination to be repaired.

Although the invention has been discussed in connection with inspecting concrete structures, other applications are also possible. For example, aluminum bridge decks are known in the art. Such bridge decks include a thick coating, which can present a hazard if the bond between the coating and aluminum is broken. The invention is believed to be useful for detecting this problem as well.

Still further applications of the invention include inspection of parking garages, foundations, tunnel walls, etc. In some of these applications, such as inspection of tunnel walls, dragging a chain across a vertical surface to excite the structure will not prove practical or possible. An alternative is to excite the structure with times such as times of a rake. Because the times are stiff, the problems associated with using chains on a vertical structure are overcome. For such applications, it may be desirable to mount the inspection device on a movable arm rather than a wheeled platform.

The embodiments described above perform data acquisition and processing in real time so results can be displayed to an operator while operating such an embodiment. Some embodiments include a marking system (such as a paint spray gun) under the control of the processor. These embodiments will mark the structure at the locations of defects as they are detected. Other embodiments of the invention simply record the signal from the microphone on a storage medium such as a magnetic tape. The recorded signal may then be analyzed at a later time and/or at a remote location.

While the invention has been described in detail in connection with the preferred embodiments known at the time, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Accordingly, the invention is not to be seen as limited by the foregoing description, but is only limited by the scope of the appended claims.

What is claimed is:

1. A method for detecting defects in a structure comprising the steps of:
    exciting the structure by direct physical contact with the structure by moving an object across the structure;
    receiving acoustical energy generated by the structure while the structure is being excited over a period of time with an acoustical sensor that is not physically coupled to the structure;
    processing a signal received from the sensor over the period of time to remove frequencies that do not correspond to defects to be detected;
    examining the processed signal to determine the presence of a defect; and
    wherein defects in the structure are detected from acoustic waves resulting from vibration of the structure.

2. The method of claim 1, wherein the exciting step is performed by continuously exciting the structure.

3. The method of claim 1, wherein the exciting step is performed by exciting the structure with broadband noise.

4. The method of claim 1, wherein the exciting step is performed using an impulse load.

5. The method of claim 1, wherein the examining step includes the step of calculating the mean square of the signal.

6. The method of claim 5, wherein the mean square of the signal is compared to a threshold to determine the presence of a defect.

7. The method of claim 6, further comprising the step of displaying the mean square of the signal on a display device.

8. The method of claim 7, wherein the exciting, receiving, processing and examining steps are performed for a plurality of time periods, each of the time periods corresponding to different portions of the structure.

9. The method of claim 8, wherein the time periods are of equal length.

10. The method of claim 8, further comprising the step of displaying a graph of the processed energy, the graph having a first axis representing a position along a length of the structure and a second axis representing a position along a width of the structure.

11. The method of claim 10, wherein color is used to represent the mean square in a time period.

12. The method of claim 1, further comprising the step of transforming the acoustical energy from the time domain to the frequency domain.

13. The method of claim 12, wherein the transforming step is performed using a Fourier transform.

14. The method of claim 1, wherein frequencies below approximately one kilohertz are removed in the processing step.

15. The method of claim 1, wherein frequencies above approximately six kilohertz are removed in the processing step.

16. The method of claim 1, wherein the structure is concrete.

17. The method of claim 1, wherein the examining step is performed by a neural network that compares a signal from a known good structure to a signal from a structure being inspected, calculates a distance measurement between the signal from the known good structure and the structure being inspected, and compares the distance measurement to a threshold.

18. The method of claim 17, further comprising the step of calculating linear prediction coefficients from the signal from the structure being inspected, wherein the distance measurement is a measurement of a difference between linear prediction coefficients from the signal from the structure being inspected and linear prediction coefficients from the known good structure.

19. A method for inspecting a concrete structure comprising the steps of:

dragging a chain across the structure;

receiving with a microphone not physically coupled to the structure sounds generated by the structure while the chain is being dragged;

digitizing a signal from the microphone;

processing the digitized signal to remove frequencies outside a frequency range of interest;

calculating the mean square of the processed signal;

comparing the mean square of the processed signal to a threshold to determine whether a defect is present in the structure; and wherein defects in the structure are detected from acoustic waves resulting from vibration of the structure.

20. An apparatus for detecting the presence of a defect in a structure, the apparatus comprising:

a mobile platform;

an excitation device mounted to the platform such that the excitation device excites the structure when the platform is in close proximity to the structure by moving an object across the structure;

a microphone mounted on the mobile platform such that the microphone is not physically coupled to the structure and is positioned to receive acoustical energy form the structure; and a processor connected to the microphone, the processor being configured to process a signal received from the microphone over a period of time to remove frequencies that do not correspond to defects to be detected and compare the processed signal to a threshold;

wherein defects in the structure are detected from acoustic waves resulting from vibration of the structure.

21. The apparatus of claim 20, wherein the processor is further configured to transform the signal received from the microphone from the time domain to the frequency domain.

22. The apparatus of claim 21, wherein a Fourier transform is used to transform the signal received from the microphone.

23. The apparatus of claim 22, wherein the processor is further configured to calculate the mean square of the signal received over the period of time.

24. The apparatus of claim 20, further comprising a sound dampening box having an open end, the box being mounted on the mobile platform, the open end facing the structure, the microphone being mounted in the box.

25. The apparatus of claim 24, further comprising a wheel attached to the platform and an odometer attached to the wheel and connected to the processor for correlating the time period to a location on the structure.

26. The apparatus of claim 25, further comprising a display device connected to the processor, the processor being further configured to display the processed signal.

27. An apparatus for inspecting a concrete structure, the apparatus comprising:

a cart;

a sensor attached to the cart and connected to a processor;

a sound dampening box mounted to the cart, the sound dampening box having an open end, the sound dampening box being positioned such that the open end faces a surface of structure to be inspected when the cart is moved across the surface;

a plurality of chains attached to the cart, the chains being positioned to drag on the surface when the cart is moved across the surface;

a microphone mounted in the box and positioned such that the microphone is not in contact with the surface when the cart is moved across the surface;

an amplifier connected to the microphone;

an analog to digital converter connected to the amplifier;

a processor connected to the analog to digital converter, the processor being configured to perform the steps of processing the signal from the converter to remove frequencies outside of a frequency range of interest, calculating a mean square of the processed signal, comparing the mean square of the signal to a threshold to determine whether a defect is present, and correlating signal to a location on the surface using the sensor; and a display connected to the processor for displaying a location of a defect;

wherein defects in the structure are detected from acoustic waves resulting from vibration of the structure.

28. The apparatus of claim 27, wherein the sensor is a global positioning sensor.

29. The apparatus of claim 27, wherein the sensor is an odometer.

\* \* \* \* \*